United States Patent
He

(10) Patent No.: US 10,921,257 B2
(45) Date of Patent: Feb. 16, 2021

(54) METHOD AND SYSTEM OF PESTICIDE DETECTION USING SERS

(71) Applicant: The University of Massachusetts, Boston, MA (US)

(72) Inventor: Lili He, Belchertown, MA (US)

(73) Assignee: University of Massachusetts, Boston, MA (US)

( * ) Notice: Subject to any disclaimer, the term of this patent is extended or adjusted under 35 U.S.C. 154(b) by 254 days.

(21) Appl. No.: 15/793,120

(22) Filed: Oct. 25, 2017

(65) Prior Publication Data

US 2018/0113075 A1 Apr. 26, 2018

Related U.S. Application Data

(60) Provisional application No. 62/412,565, filed on Oct. 25, 2016.

(51) Int. Cl.
| | | |
|---|---|---|
| *G01N 21/65* | (2006.01) | |
| *G01N 33/50* | (2006.01) | |
| *G01J 3/44* | (2006.01) | |
| *B82Y 15/00* | (2011.01) | |

(52) U.S. Cl.
CPC .............. *G01N 21/658* (2013.01); *G01J 3/44* (2013.01); *G01N 33/50* (2013.01); *B82Y 15/00* (2013.01)

(58) Field of Classification Search
CPC ......... G01N 21/658; G01N 33/50; G01J 3/44; B82Y 15/00
See application file for complete search history.

(56) References Cited

U.S. PATENT DOCUMENTS

| 2010/0087723 A1* | 4/2010 | Van Duyne ........ A61B 5/14532 600/365 |
| 2016/0076086 A1* | 3/2016 | Vo-Dinh .............. C12Q 1/6825 424/490 |

OTHER PUBLICATIONS

Shen, Aiguo et al. "Surface-enhanced Raman spectroscopy in living plant using triplex Au—Ag—C core-shell nanoparticles." Journal of Raman Spectroscopy (2011) 42 879-884. (Year: 2011).*
Shen, Aiguo et al. "Triplex Au—Ag—C core-shell nanoparticles as a novel Raman label." Advanced Functional Materials (2010) 20 969-975. (Year: 2010).*
Palonpon, Almar F. et al. "Raman and SERS microscopy for molecular imaging of live cells." Nature (2013) 8 677-692. (Year: 2013).*
Toprak, Erdal et al. "Three-dimensional particle tracking via bifocal imaging." Nano Letters (2007) 7 2043-2045. (Year: 2007).*
Hou, Ruyan, et al., "In situ SERS detection of multi-class insecticides on plant surfaces", Anal. Methods, 2015, 7,, (Jun. 28, 2015), 6325-6330.
Xu, Meng-Lei, et al., "Detection of Pesticide Residues in Food Using Surface-Enhanced Raman Spectroscopy: A Review", J. Agric. Food Chem. 2017, 65, (2017), 6719-6726.

* cited by examiner

*Primary Examiner* — Christopher Adam Hixson
(74) *Attorney, Agent, or Firm* — Schwegman Lundberg & Woessner, P.A.

(57) ABSTRACT

The present disclosure provides a method for mapping one or more analytes that contact a biological structure. The method uses surface-enhanced Raman spectroscopy and includes contacting the biological structure and a metallic nanoparticle. The method further includes collecting a spectrum with a Raman spectrometer. The method further includes determining a location of the analyte along at least one of an x-direction, a y-direction and a z-direction on the structure.

20 Claims, 5 Drawing Sheets
(5 of 5 Drawing Sheet(s) Filed in Color)

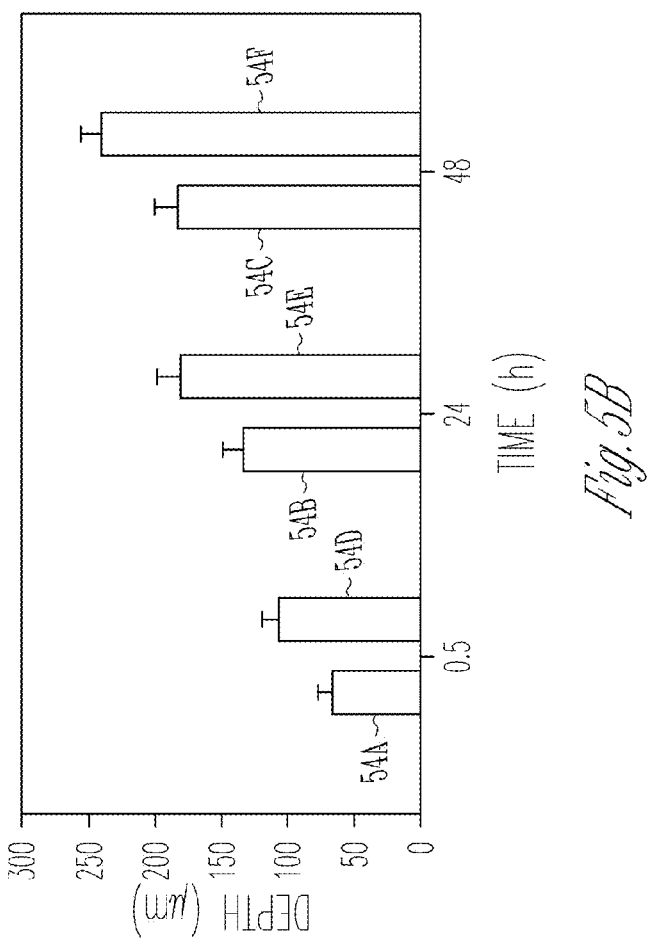
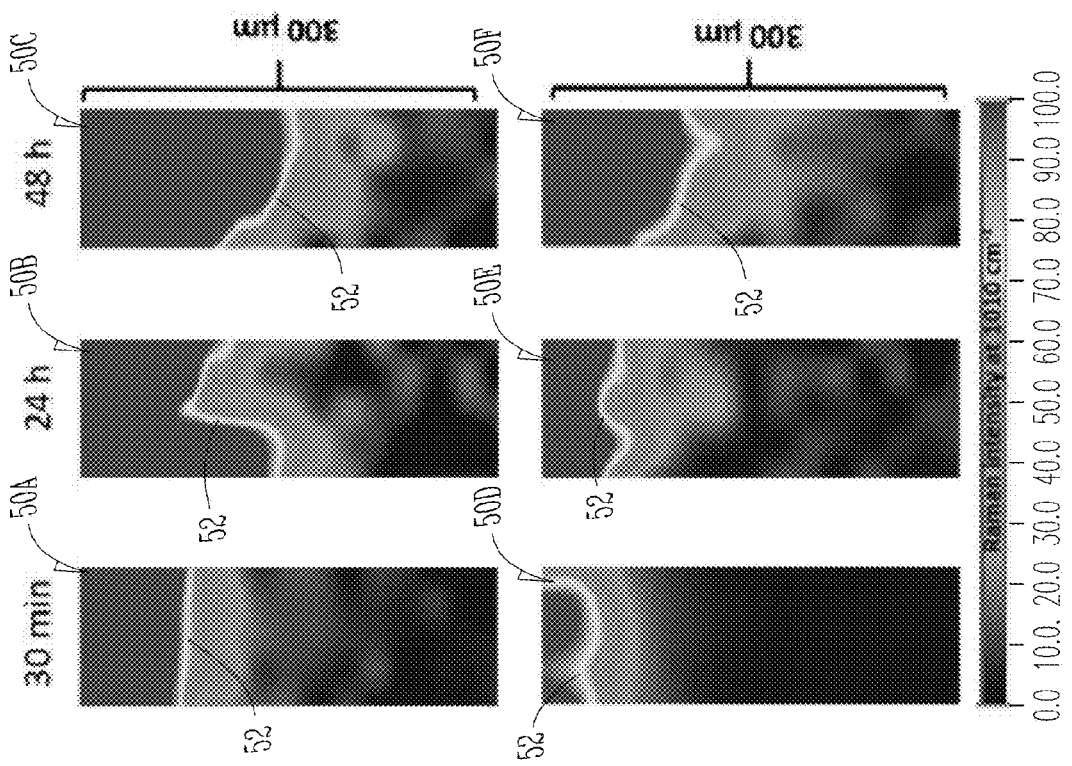
Fig. 5A
Fig. 5B

METHOD AND SYSTEM OF PESTICIDE DETECTION USING SERS

CROSS-REFERENCE TO RELATED APPLICATION

This application claims the benefit of priority to U.S. Provisional Patent Application Ser. No. 62/412,565 entitled "Method and System of Pesticide Detection Using SERS," filed Oct. 25, 2016, the disclosure of which is incorporated herein in its entirety by reference.

STATEMENT OF GOVERNMENT SUPPORT

This invention was made with Government support under 2016-67017-24458 awarded by the United States Department of Agriculture National Institute of Food and Agriculture (USDSA-NIFA) and under 2010-ST-061-FD0001 awarded by the Department of Homeland Security—Science and Technology. The U.S. Government has certain rights in this invention.

BACKGROUND

Surface enhanced Raman spectroscopy (SERS) can provide complementary spectroscopic data for analytes. However, a problem with SERS is that it can be limited to merely detecting the presence of an analyte of interest. In some applications, it may be desirable to not only detect the presence of an analyte but to determine the location of the analyte in three dimensional space.

SUMMARY OF THE DISCLOSURE

The present disclosure provides a method for mapping one or more analytes. That contact a biological structure. The method uses surface-enhanced Raman spectroscopy and includes contacting the biological structure and a metallic nanoparticle. The method further includes collecting a spectrum with a Raman spectrometer. The method further includes determining a location of the analyte along at least one of an x-direction, a y-direction and a z-direction on the structure.

The present disclosure further provides a method for mapping one or more analytes that contact a biological structure via surface-enhanced Raman spectroscopy. The method includes contacting the biological structure with at least one elemental gold nanoparticle; collecting a spectrum with a Raman spectrometer; and detecting a location of a pesticide along at least one of an x-y direction and a z-direction on the structure.

The present disclosure further provides an assembly. The assembly includes a plant tissue and one or more analytes contacting the plant tissue. The assembly further includes at least one metallic nanoparticle that contacts the biological structure. The assembly further includes a Raman microscope configured to detect a location of the analyte along at least one of an x-direction, a y-direction and a z-direction on the structure.

There are various advantages to using the methods and assemblies disclosed herein, some of which are unexpected. For example, according to various embodiments of the present disclosure it is possible to determine the location in at least one of a x-direction, a y-direction, and a z-direction of an analyte in a biological sample, as opposed to merely detecting the presence of an analyte. According to various embodiments of the present disclosure, this can help to determine the level of penetration an analyte has reached in a biological sample. According to various embodiments of the present disclosure, this can help to determine how safe an edible product including the analyte is to consume. According to various embodiments of the present disclosure, being able to determine the location of the analyte can help to determine the effectiveness of the analyte (e.g., if the analyte is a pesticide) in protecting the biological sample. According to various embodiments of the present disclosure the analytes can penetrate deeper into the biological structure than a corresponding analyte or sample that is free of metallic nanoparticles. According to various embodiments if the biological sample is an animal tissue the method and assemblies can be used to detect the presence and location of an analyte in the animal. According to various embodiments of the present invention, the stability of the analyte can measured over time by detecting the presence or disappearance of the analyte.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

The patent or application file contains at least one drawing executed in color. Copies of this patent or patent application publication with color drawing(s) will be provided by the Office upon request and payment of the necessary fee.

Figure 1:
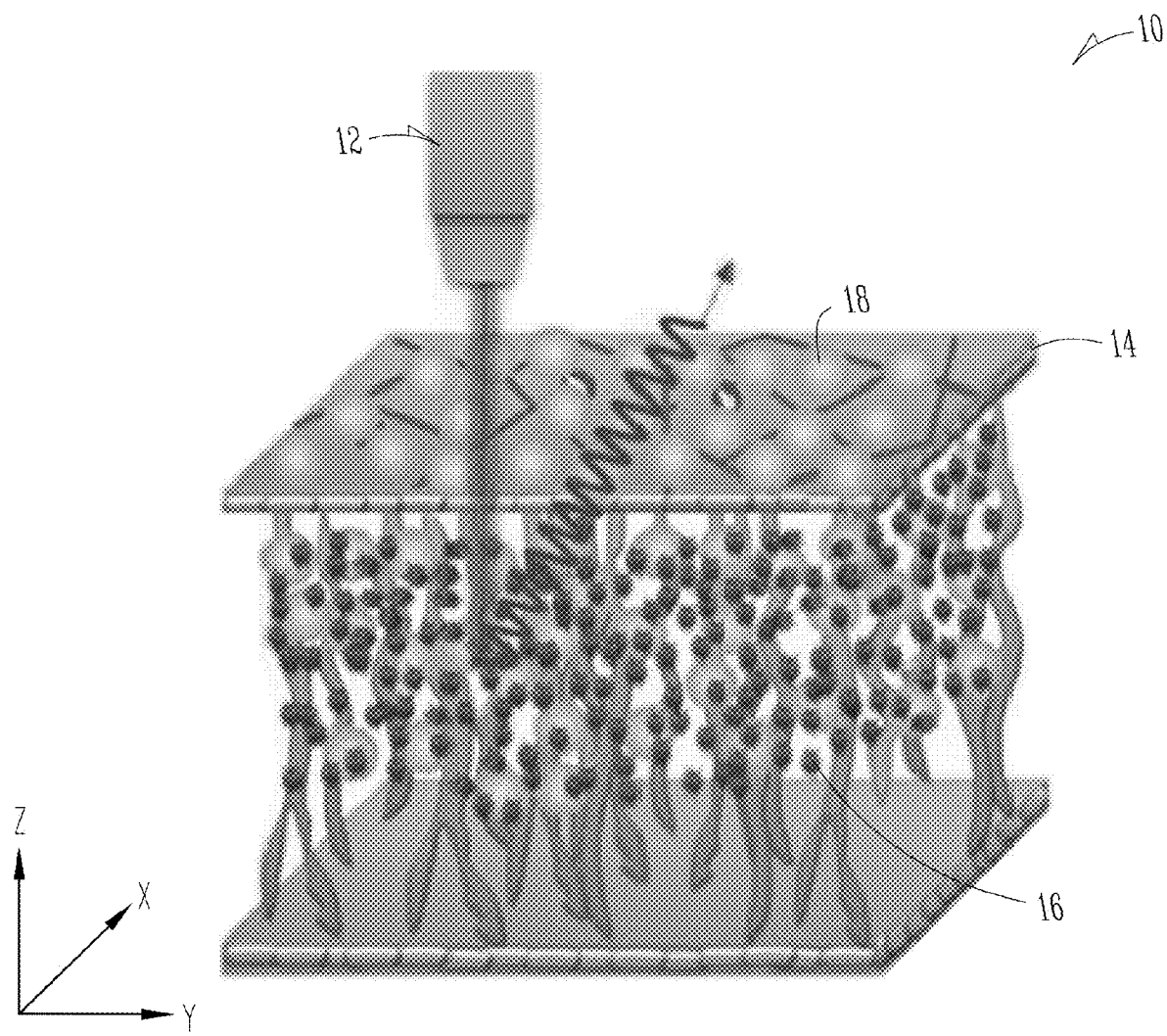

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1 is a schematic depiction of an assembly 10, in accordance with various embodiments.

Figure 2:
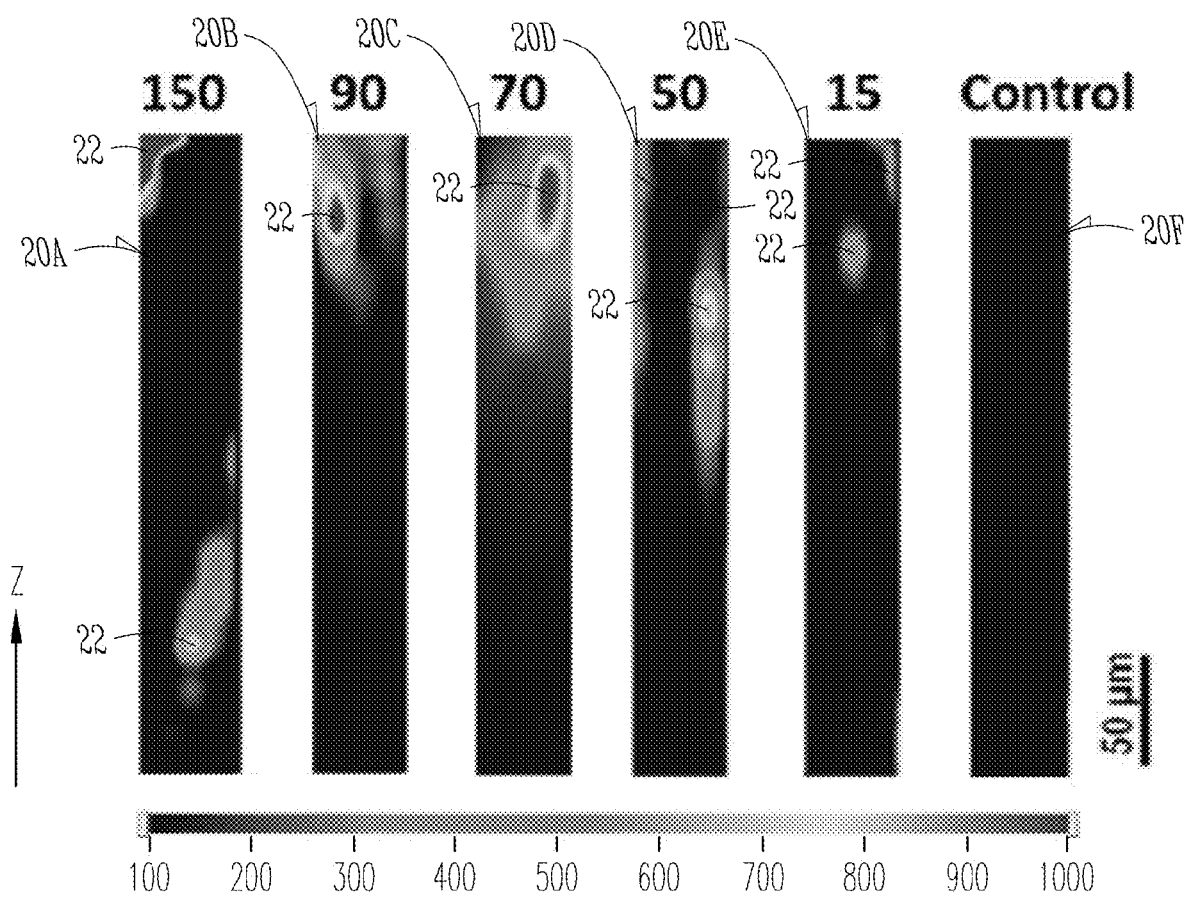

FIG. 2 shows spectra of a plant tissue generated through surface-enhanced Raman spectroscopy when a metallic particle is varied by particle size, in accordance with various embodiments.

Figure 3:
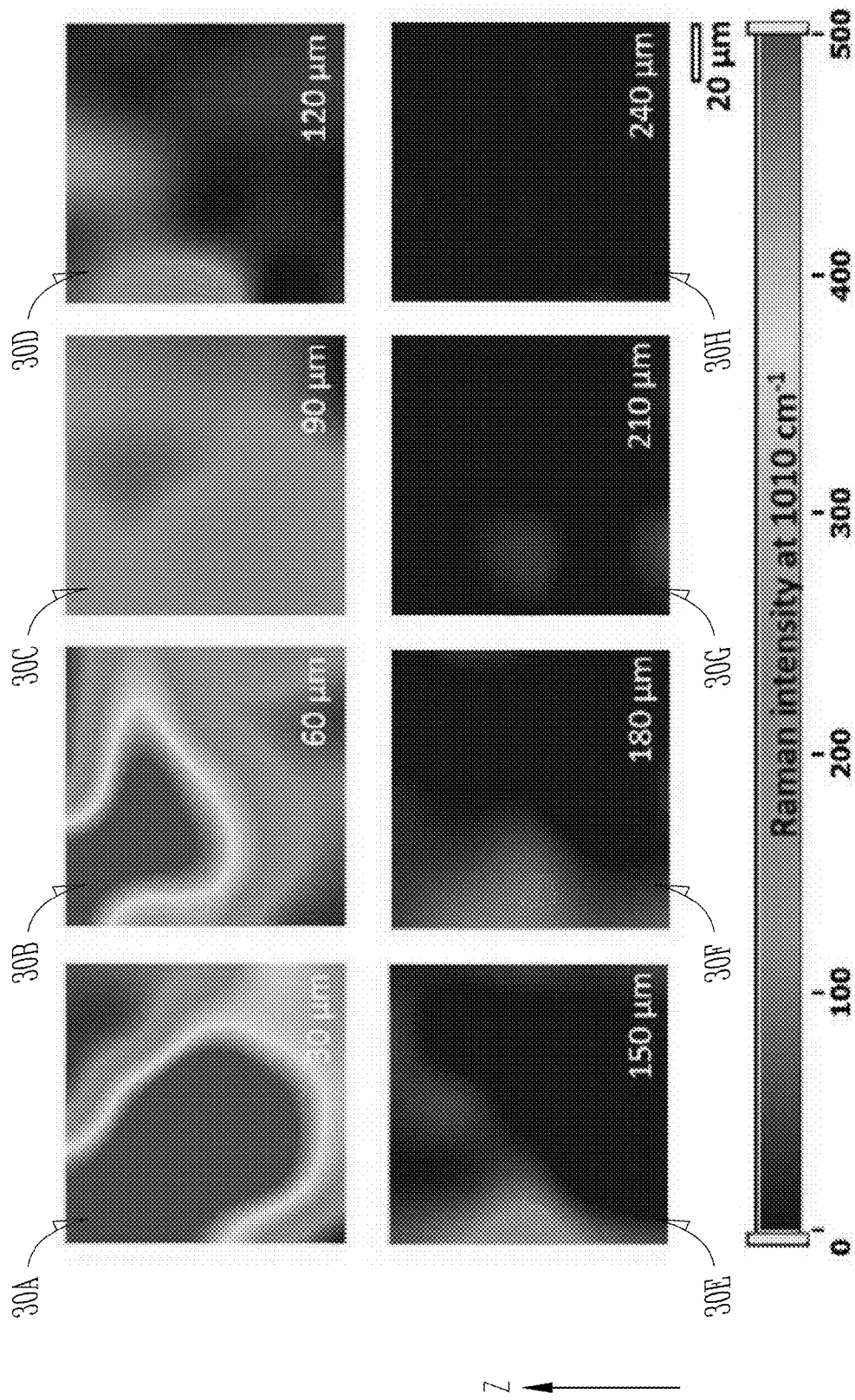

FIG. 3 shows spectra of a plant tissue generated through surface-enhanced Raman spectroscopy when a metallic nanoparticle is located a different depths in the biological sample, in accordance with various embodiments.

Figure 4A:
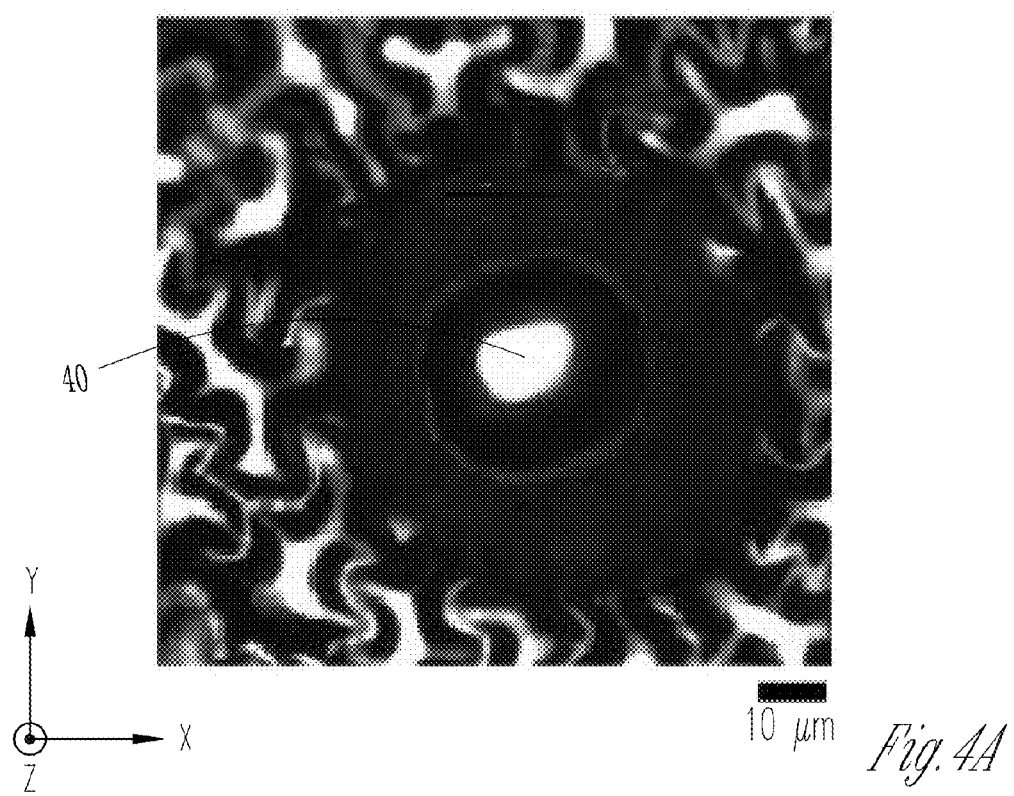

FIG. 4A is a scanning electron microscope image of a section of a plant tissue, in accordance with various embodiments.

Figure 4B:
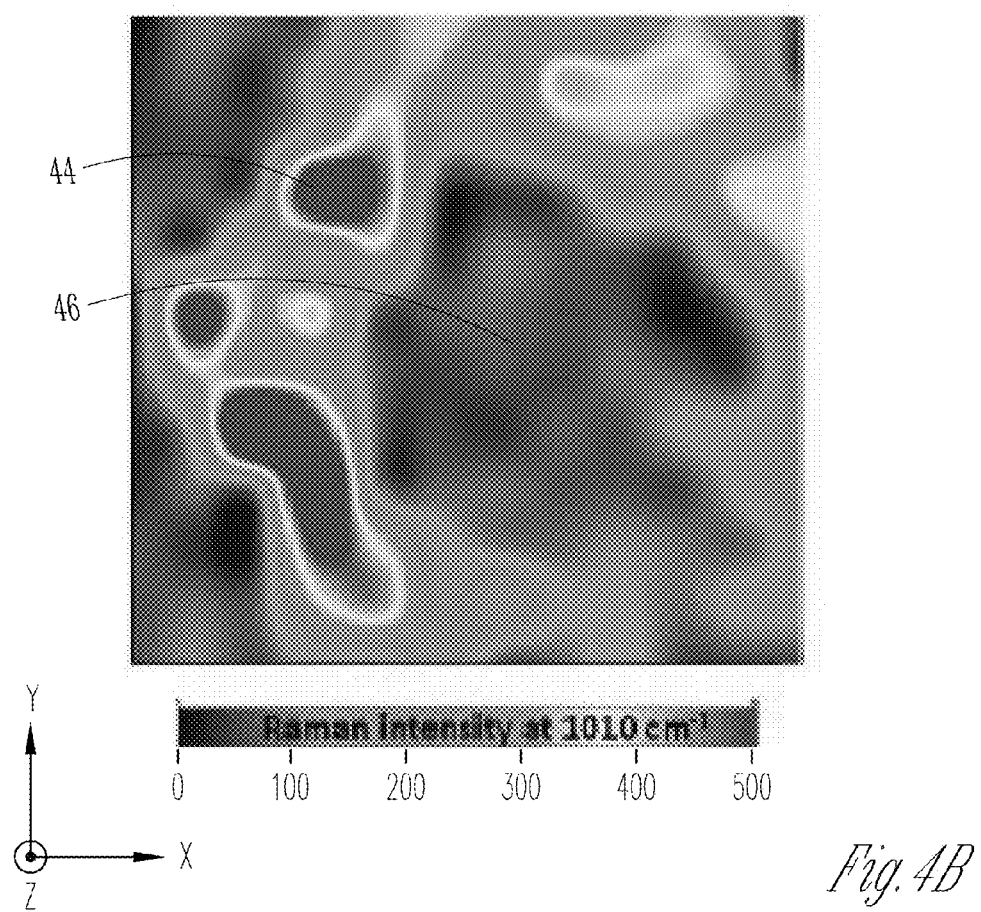

FIG. 4B, is a spectrum of the plant tissue of FIG. 4A generated through surface-enhanced Raman spectroscopy, in accordance with various embodiments.

FIG. 5A shows spectra of a plant tissue generated through surface-enhanced Raman spectroscopy when a metallic nanoparticle is exposed to a tissue for variable time lengths, in accordance with various embodiments.

FIG. 5B is a bar graph showing the penetration of the metallic nanoparticles of the spectra of FIG. 5A, in accordance with various embodiments.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

According to various embodiments of the present disclosure, an assembly for detecting and mapping a location of at least one analyte in a biological sample is described. FIG. 1 is a schematic depiction of an assembly 10. The assembly includes a Raman microscope 12 positioned in optical communication with a biological structure 14. The biological structure includes one or more metallic nanoparticles 16 and analytes 18.

The Raman microscope is one that is capable of performing surface-enhanced Raman spectroscopy. Surface-enhanced Raman spectroscopy is a surface-sensitive technique that enhances Raman spectroscopy by molecules adsorbed on metal surfaces or by nanoparticles. The enhancement factor can be as much as $10^{10}$ to $10^{11}$ compared to standard Raman spectroscopy, which means the technique may detect single molecules. Beyond detecting the presence of molecules, such as an analyte, the present disclosure illustrates methods for determining or mapping the location in three-dimensional space of the analyte.

By mapping the location of the analyte in three-dimensional space, it is meant that the location of the analyte in the biological structure can be determined along an x-direction, a y-direction, and a z-direction. As shown in FIG. 1, the location of the analyte in the z-direction can correlate to the penetration of the analyte relative to the thickness of the biological structure (e.g., in a vertical direction). The location of the analyte in the x-direction and the y-direction can correlate to the location of the analyte in a horizontal direction relative as shown in FIG. 1.

In operation, the biological structure can be a plant or an animal tissue. Examples of plant tissues can include a leaf, a flower, fruit surface, stem, or a root. Examples of animal tissues can include skin. As generally understood, a tissue includes an aggregate of similar cells and cell products forming a definite kind of structural material with a specific function, in a multicellular organism.

The metallic nanoparticle contacts the biological sample. The metallic nanoparticle can be present on a surface of the biological sample or be located within (e.g., penetrated) the biological sample. The metallic nanoparticle is selected from a metallic nanoparticle that is active in surface-enhanced Raman spectroscopy. By active it is meant that the metallic nanoparticle enhances the signal of an analyte in Raman spectroscopy. Examples of suitable metallic nanoparticles include a material chosen from $Ag_2O$, elemental silver, elemental gold, elemental copper, elemental platinum, alloys thereof, and mixtures thereof. While these are suitable examples, elemental gold has been found to be a particularly suitable material. Any assembly or method according to this disclosure can a plurality of the metallic nanoparticles. The plurality of metallic nanoparticles can each include the same material. Alternatively at least two of the metallic nanoparticles can include a different material.

The morphology of an individual metallic nanoparticle can be any suitable morphology. For example, the metallic nanoparticle can be substantially spherical. The metallic nanoparticle can also have an irregular or substantially amorphous shape. In some examples, that include a plurality of metallic nanoparticles, a major portion of the individual metallic nanoparticles can be substantially spherical. For example, approximately 80% to about 100% of the metallic nanoparticles can have a substantially spherical morphology.

A particle size of the individual metallic nanoparticle is in a range of from about 20 nm to about 200 nm, about 40 nm to about 60 nm, or less than, equal to, or greater than about 20 nm, 30, 40, 50, 60, 70, 80, 90, 100, 110, 120, 130, 140, 150, 160, 170, 180, 190, or about 200 nm. The "particle size" of the individual metallic nanoparticle refers to the largest dimension of the metallic nanoparticle. For example, the largest dimension of the metallic nanoparticle can refer to a diameter, width, or height of the metallic nanoparticle. In some examples including a plurality the metallic nanoparticles, a first metallic nanoparticle can have a particle size in a largest dimension that is different from a particle size in a largest dimension of a second nanoparticle.

The analyte can be any non-naturally occurring compound in the biological structure. The non-naturally occurring compound should be a compound that has some Raman spectroscopy activity (e.g., can be used to generate a Raman spectroscopy spectrum). Examples of analytes can include a pesticide (including, for example, a fungicide, an insecticide, a herbicide) an antibiotic, and a mixture thereof. In some examples the biological sample can include mixtures of different pesticides or antibiotics. Examples of pesticides can include thiabendazole, ferbam, phosmet, acetamiprid, fonofos, isocarbophos, phorate, deltamethrin, imidacloprid, and mixtures thereof.

To perform a method for mapping the one or more analytes, using surface-enhanced Raman spectroscopy, a user may contact the biological structure with the one or more metallic nanoparticles. In order to properly enhance the signal of the analyte the metallic nanoparticles are positioned proximate to the analytes. For example, a distance between an adjacent metallic nanoparticle and the analyte can be in a range of from about 0.10 nanometers to about 20 nanometers, about 0.10 nanometers to about 5 nanometers, or less than, equal to, or greater than about 0.10 nanometers, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or about 20.0 nm. In some examples, the metallic nanoparticle and the analyte react to form a complex.

The metallic nanoparticle and the analyte can interact on an exterior surface of the biological sample or in the interior of the biological sample. If a user does not want to collect a spectrum of the analytes on the surface of the biological sample, the sample can be washed (e.g., with water) prior to contact with the metallic nanoparticle.

A spectrum of the metallic nanoparticle can be collected immediately or after a predetermined about of time. Collecting the spectrum immediately can be helpful to collect signals of the analyte on the surface of the biological sample. However, if the spectrum is collected after a set amount of time the metallic nanoparticle can have a chance to penetrate the biological sample. The particle size of the metallic nanoparticle can impact its ability to penetrate the biological sample. For example, the smaller particle size metallic nanoparticles may be able to penetrate deeper in the biological sample than metallic nanoparticles having a larger particle size. However, metallic nanoparticles having larger particle sizes may yield stronger signals.

After a predetermined amount of time, a spectrum is collected. The spectrum is used to determine a location of the analyte along at least one of an x-direction, a y-direction and a z-direction on the structure. FIG. 2 shows spectrums 20A, 20B, 20C, 20D, 20E, and 20F. Each spectrum shows the location 22 of an analyte in a biological sample having a thickness in a z-direction or 50 µm. In spectrums 20A-20F, the metallic nanoparticles are elemental gold. In spectrum 20A the gold nanoparticles have a diameter of 150 nm, in spectrum 20B the gold nanoparticles have a diameter of 90 nm, in spectrum 20C the gold nanoparticles have a diameter of 70 nm, in spectrum 20D the gold nanoparticles have a diameter of 50 nm, and in spectrum 20E the gold nanoparticles have a diameter of 15 nm. Spectrum 20F is a control that includes an analyte but does not include elemental gold nanoparticles. As can be seen from the spectra, the location of the analyte in the z-direction can be shown with this method. While different particle sizes of the elemental gold nanoparticles can result in different penetration depths or signal intensities it was found that elemental gold nanoparticles having a diameter of about 50 nm shows good overall performance (e.g., sufficient penetration and signal strength).

The methods and systems disclosed herein can function over a great degree of depths beyond 50 µm. FIG. 3 shows spectrums 30A, 30B, 30C, 30D, 30E, 30F, 30G, and 30H. Spectrums 30A-H show images of analytes taken at different depths. Spectrum 30A is taken at 30 µm, spectrum 30B is taken at 60 µm, spectrum 30C is taken at 90 µm, spectrum 30D is taken at 120 µm, spectrum 30E is taken at 150 µm, spectrum 30F is taken at 180 µm, spectrum 30G is taken at 210 µm, and spectrum 30H is taken at 240 µm.

While the method can be used to detect and locate the analyte in the z-direction. The method can also be used to detect the present of an analyte in an x-direction as well as a y-direction. FIG. 4A is a scanning electron microscope image of a section of a plant tissue. One constituent of the plant tissue is gland 40. FIG. 4B, is a spectrum taken, using the instantly disclosed methods. FIG. 4B shows locations 42 of the analytes in the x-direction and y-direction FIG. 4B, further shows gap 46 denoting the location of gland 40.

The extent of penetration by the metallic nanoparticles in the biological sample can be a function of the amount of time that the metallic nanoparticle is exposed to the sample. FIG. 5A shows spectrums 50A, 50B, 50C, 50D, and 50E. Spectrum 50A, shows the penetration of the metallic nanoparticle generating image 52 in a live biological sample after 30 minutes. Spectrum 50B, shows the penetration of the metallic nanoparticle generating image 52 in a live biological sample after 24 hours. Spectrum 50C, shows the penetration of the metallic nanoparticle generating image 52 in a live biological sample after 48 hours. Spectrum 50D, shows the penetration of the metallic nanoparticle generating image 52 in a harvested biological sample after 30 minutes. Spectrum 50E, shows the penetration of the metallic nanoparticle generating image 52 in a harvested biological sample after 24 hours. Spectrum 50F, shows the penetration of the metallic nanoparticle generating image 52 in a harvested biological sample after 48 hours. FIG. 5B is a bar graph showing the penetration of the metallic nanoparticles of spectra 50A-50F. Bar 54A corresponds to (e.g., shows the penetration depth at which an image 52 is generated) to spectrum 50A, bar 54B corresponds to spectrum 50B, bar 54C corresponds to spectrum 50C, bar 54D corresponds to spectrum 50D, bar 54E corresponds to spectrum 50E.

EXAMPLES

Various embodiments of the present disclosure can be better understood by reference to the following Examples which are offered by way of illustration. The present disclosure is not limited to the Examples given herein.

Example 1

Further details of this Example can be found in the article "Real-time and in situ monitoring of pesticide penetration in edible leaves by surface-enhanced Raman scattering mapping", *Anal. Chem.* 2016, 88, 5243-5250, the contents of which, including supporting information is hereby incorporated by reference.

Iron(III) dimethyldithiocarbamate (fungicide ferbam) and 2-(4-Thiazolyl) benzimidazole (fungicide thiabendazole) were of analytical reagent grade and were purchased from Sigma-Aldrich (St. Louis, Mo.). Sodium bicarbonate ($NaHCO_3$) was purchased from Fisher Scientific (Pittsburgh, Pa.). Citrate-capped AuNPs colloids were purchased from NANO PARTZ™ Inc. (Loveland Colo., USA). Organic baby spinach leaves were obtained from Whole Foods Market (Waltham, Mass.). All reagents were used without further purification. Ultrapure water (18.2 MΩ·cm) was produced with Thermo Scientific Barnstead Smart2Pure Water Purification System and used for the preparation of all solutions.

Spinach leaves were chosen as the model edible plant tissue due to its high association with pesticide exposure, high consumption in the US, and relative large and flat surfaces for experiment. These leaves were carefully washed with ultrapure water and dried before experimentation. Ferbam and thiabendazole were used as examples of non-systemic and systemic pesticide, respectively, and each was prepared in water with various concentrations. A volume of 50 μL of each solution was then mixed with 50 μL of a 250 ppm 50 nm AuNPs solution for 1 min. at room temperature to ensure complete pesticide complexation with AuNPs through Au-thiol bond. 5 μL of each of the pre-prepared pesticide solution were then pipetted onto spinach leaves situated on a glass slide and air-dried in a fume hood for 30 min. Solutions of AuNPs without pesticide, ferbam alone and thiabendazole alone were also pipetted onto spinach leaves as control treatments for comparisons. All controls were air-dried in a fume hood as above. For evaluation of feasibility of Raman detection of pesticides on spinach leaves, 5 μL of the pre-prepared pesticide solution and AuNPs solution without pesticide were also dropped onto a gold slide and dried for 30 min in a hood for comparisons. Raman spectra were collected individually for all treatments.

To study non-systemic pesticide penetration, 20 ppm of ferbam was chosen as a model and the concentration of 20 ppm solution is about 7 mg/kg (7 ppm) on spinach leaves. Twenty ppm was chosen because this concentration is around maximum residue limits (MRL). From a viewpoint of useful guidance for effective and safe applications of pesticides on plants, higher concentration of pesticide is more toxic and meaningful. The use of high concentration of pesticides may mimic the early stage of pesticide applications. Monitoring pesticide residues can be meaningful to ensure the good coverage of pesticides on the surfaces as well as to predict the safe date for harvest, from a farmer's perspective. In detail, a 5 μL aliquot of the 20 ppm ferbam solution was pipetted onto the surface of spinach leaves and put in a fume hood for 30 min. A 5 μL aliquot of a 250 ppm solution of AuNPs was then pipetted onto the same area of the spinach leaf where the ferbam solution had been placed. After 1 h, bright field light scattering images and SERS mapping images were collected from all samples.

In order to remove any interference caused by pesticide residues on the spinach leaf surface, different washing methods were investigated. After drying the 5 μL aliquot of the 20 ppm ferbam solution that had been pipetted onto fresh spinach leaves, leaves with ~2.0×2.0 $cm^2$ square area were cut from fresh whole leaves by a sharp knife. Then each leaf was immersed into 20 mL of deionized water or 20 mL of a 10 mg/mL of $NaHCO_3$ solution. For the water washing method, each leaf was submerged into water for either 10 or 60 min. For the $NaHCO_3$ washing method, each leaf was submerged into the $NaHCO_3$ solution for 30, 60, 90, or 120 s and then gently rinsed with 500 mL of deionized water for 30 s, respectively. All washed leaf samples were air-dried at room temperature for 30 min before being treated with AuNPs. After AuNPs solution for drying 30 min, SERS detection was performed on that area. Ten discrete locations were randomly chosen in each leaf sample and scanned. Similar samples without either washing method were also scanned for comparisons.

The penetration behavior of ferbam was monitored during different time periods from 2 hours to 2 days. A 5 μL aliquot of the 20 ppm ferbam solution was pipetted onto leaves and allowed to dry in air at room temperature over different time intervals. Following different exposure periods, the surface residues of ferbam were washed with $NaHCO_3$ solution and a 5 μL aliquot of the 250 ppm AuNPs solution added as described above. After 1 h for drying, SERS depth mapping images were obtained using the confocal Raman instrument. Similar samples without washing were likewise measured for comparison purposes.

To study accurate systemic pesticide penetration, different washing methods were also used to remove surface thiabendazole residues. Washing treatments were carried out using either water or $NaHCO_3$ solution. For the water washing method, each thiabendazole contaminated leaf was submerged into water for either 10 or 60 min. For the $NaHCO_3$ washing method, each contaminated leaf was submerged into the $NaHCO_3$ solution for 60 s, 90 s, 120 s or 150 s and then gently rinsed with 500 mL of deionized water for 30 s, respectively. Following the $NaHCO_3$ washing method, the leaves were gently rinsed by water for 30 s. Surface thiabendazole residues were then analyzed by pipetting 5 μL of a 250 ppm AuNP solution onto the same leaf area where thiabendazole had been placed prior to washing and determining SERS depth mapping images by Raman instrument as before. The penetration behaviors of thiabendazole were also monitored during different time periods as for ferbam above.

A DXR Raman microscope (Thermo Fisher Scientific, Madison, Wis., U.S.A.) with a 780 nm laser and a 20× long distance microscope objective was used in this Example. Each spectrum was scanned from 400 to 2000 $cm^{-1}$ with 5 mW laser power and 2 s exposure time. For measuring pesticides on both gold slides and spinach leave surfaces, Raman mapping was applied with a 50 μm slit aperture to maximize the signals. Ten discrete locations were randomly chosen on each sample for analysis. For penetration studies, SERS depth mapping images were obtained with a 50 μm pinhole aperture to control the confocal depths using a scanning depth of 300 μm. Each area was randomly picked up from spinach leaves and vertical to leaves surface with 100 μm×300 μm area. The step size of the mapping was 20 μm and one image contained 75 scanning spots. Raman images were integrated based on the characteristic peaks in the pesticide spectra using the atlμs function in the OMINCS software (Thermo Fisher Scientific).

Previous NPs-plant interaction research determined that AuNPs could rapidly penetrate into plant tissues. The penetration of AuNPs of different diameters into leaves were investigated using the in situ SERS mapping technique. The corresponding Raman images were integrated based on the characteristic peak at 1525 $cm^{-1}$. Penetration of AuNPs, as observed, started immediately upon pipetting the AuNPs colloids onto the spinach leaf surface. The size of NPs was important for both signal intensity and penetration depth. 15 nm AuNPs had relatively weak signals compared with 50, 70, 90, 150 nm AuNPs, and their signals were lost when they penetrated further than 75 μm. 50 nm AuNPs penetrated to 150 μm within 40 min, further than 70, 90 or 150 nm AuNPs. For 150 nm AuNPs we observed a part of signal at a depth of 250 μm, which is probably due to the various size of 150 nm AuNPs prepared. From this data, we chose 50 nm AuNPs as the probe for studying pesticide penetration.

The SERS spectra of ferbam and thiabendazole using 50 nm AuNPs were obtained on both the gold coated microscopic slides and spinach leaf surface). The characteristic SERS peaks of ferbam were clearly detected at 1371, 1138, 940 and 553 $cm^{-1}$. The signature peaks for thiabendazole were found at 1275, 1010 and 780 $cm^{-1}$. Little or no signals were detected from AuNPs, ferbam and thiabendazole without mixing with AuNPs, or with spinach leaves alone. Moreover, there was not any measurable pesticide from organic spinach leaves obtained. The concentration-dependent SERS spectra of ferbam on spinach leaves were obtained with increasing concentration from 1 ppb to 100 ppm. The control was spinach leaves without ferbam exposure. Even as low as 1 ppb, Raman signals of ferbam can still be clearly seen, showing the ultra-high sensitivity of the developed SERS method for the detection of ferbam with the detection limit of 1 ppb. Similarly SERS spectra of thiabendazole on spinach leaves with increasing concentration from 2 ppb to 100 ppm and the detection limit were determined to be 2 ppb. The ultra-high sensitivity detection of characteristic Raman signatures of pesticides demonstrate the successful application and the feasibility of using AuNPs for the analysis of ferbam and thiabendazole on spinach leaves. The peaks 1317 $cm^{-1}$ for ferbam and 1010 $cm^{-1}$ for thiabendazole were chosen as the characteristic peaks for monitoring and image integration in the following studies.

In an in situ method for analyte detection, the inventors pipetted ferbam on the spinach leaf surface followed by the addition of AuNPs colloids. In an alternative protocol, a washing step was employed to remove the surface pesticide residues before applying the AuNP colloids. In detail, an aliquot of 20 ppm ferbam solution was first pipetted onto the spinach leaf surface. Subsequently, the leaf was submerged into the washing solution over a period of time and then gently rinsed with deionized water. Before Raman measurements, AuNPs were pipetted onto the same area of the spinach leave where the ferbam solution had been placed. For the leaf surface without washing, a mapping image shows the fingerprint information of ferbam molecules. These results illustrate a clear penetration of ferbam molecules into spinach leaf at least to 100 μm depth. This finding was unexpected at the first glance as ferbam is a non-systemic pesticide, which means generally it should have little or no penetration abilities. However, it is possible that strong interactions between the ferbam and AuNPs resulted in the co-penetration of the AuNPs-ferbam complex. This finding can have three implications. Firstly, the co-penetration of the ferbam and AuNPs may bring up new toxicity issues as the penetrated AuNPs-ferbam complex may have different behaviors and toxicity. Secondly, on the positive side, if it is necessary to alter the non-systemic property of a pesticide, then AuNPs can be used as the delivering matrix for penetration. Thirdly, for this study, it became apparent that to obtain a reliable measurement of the pesticide penetration, the interference of the pesticide residue on the leaf surface would need to be eliminated. For this purpose, different washing methods were evaluated to ensure complete removal of the surface pesticide residues.

After washing the leaf surfaces using $NaHCO_3$ solution for 120 s, no characteristic ferbam signals were detected from 2 hours to 2 days following its application onto spinach leaf surfaces. This result indicates that ferbam is not able to penetrate into the spinach leaves even after 2 days' exposure. In contrast, the ferbam signals are clearly observed inside the spinach leaves without washing. The penetration depth of ferbam did not correlate to the ferbam exposure time (from 2 hours to 2 days) because the penetration of ferbam is dependent on the AuNPs penetration and this process was the same for all samples.

In order to study the penetration of systemic pesticides into spinach leaves, a washing method for the total removal of surface residues of thiabendazole was developed. As for ferbam, both water and $NaHCO_3$ solution were examined. SERS signals of thiabendazole at 1275, 1010 and 780 $cm^{-1}$ disappeared and Raman intensity of characteristic peaks of thiabendazole at 1010 $cm^{-1}$ is very weak after washing with the $NaHCO_3$ solution for 150 s. Similarly, this result indicates that the surface residues of thiabendazole is less than 2 ppb and could be considered negligible. Thus, this optimized washing method was used to study thiabendazole penetration into leaves.

Thiabendazole can penetrate into spinach leaves even though the surface pesticides had been removed, which reflects its systemic property. The earliest time of detecting thiabendazole is following 6 hours' exposure. With increasing exposure time, the penetration depths of thiabendazole gradually increased to approximately 150 μm in the depth mapping images. To more accurately estimate the penetration depth following a 2 days exposure, the selected areas (100 μm×100 μm) parallel to leaves surface were scanned at different depths. Raman images at eight different depths (30, 60, 90, 120, 150, 180, 210 and 240 μm) were observed based on the characteristic peak of thiabendazole at 1010 $cm^{-1}$. The inventors also choose the same position on different depth of mapping images and their corresponding SERS spectra. With increasing depth, the SERS signals of thiabendazole decreased from position of 1 to 8. SERS signals of thiabendazole are clearly observed from 30-210 μm in depth, while no signal was detected at the 240 μm depth, indicating that thiabendazole penetrated into spinach leaves to approximately 210 μm. For comparison, the inventors investigated thiabendazole penetration into spinach leaves without washing surface thiabendazole residues and corresponding mapping results at different exposure times. Compared with the penetration depths of pesticides in non-washing conditions are deeper than those after washing. This result may be explained by additional pesticide molecules co-penetrating with AuNPs under the non-washing condition, which allows the pesticide molecules to penetrate further or improves the sensitivity of detection due to larger amount of molecules. To study the concentration effect, various concentrations (0.2 ppm, 2 ppm and 100 ppm) of thiabendazole were tested under the same condition as for the 20 ppm concentration. With 100 ppm thiabendazole, a significantly longer time (e.g., 10 min) was needed to completely remove the surface pesticide residues. For lower concentrations of thiabendazole, a shorter time (e.g., 20 s for 2 ppm and 3 s for 0.2 ppm) were needed to completely remove the surface pesticide residues. Higher concentration of thiabendazole showed penetration faster and deeper than the lower concentration. The results obtained here demonstrate the developed SERS method has excellent feasibility for monitoring a wide range of concentrations of pesticide penetration into spinach leaves, which could meet the need to determine realistic low levels of pesticides.

To further validate thiabendazole penetration, the inventors developed another method in which they pipetted the pesticides onto one side and the AuNPs onto the other side of the leaf. After 3 days exposure, the obtained the SERS depth mapping image based on characteristic peak of thiabendazole at 1010 cm-1. No SERS signals of thiabendazole were observed in the area close to either upper surface or lower surface. Proximity to the center of the leaf, however, we found intense SERS signals of thiabendazole, indicating the penetrated thiabendozle met the penetrated AuNPs at this position. This data clearly demonstrated that thiabendazole is able to penetrate into the spinach leaves in systemic way.

Example 2

Further details of this Example are found in "Evaluation of the penetration of multiple classes of pesticides in fresh produce using surface-enhanced Raman scattering mapping", *Journal of Food Science, Col* 81, Nr. 11, 2016, the contents of which, including supplemental materials are hereby incorporated by reference. Thiabendazole (fungicide: 2-(4-thiazolyl)-1H-benzimidazole, ≥99%), acetamiprid (insecticide: (E)-N-[(6-chloro-3-pyridyl)methyl]-N'-cyano-N-methylethanimidamide, analytical grade), ferbam (fungicide: Iron(III) dimethyldithiocarbamate, analytical grade) and phosmet (insecticide: O,O-dimethyl S-Phthalimido Methyl Phosphorodithioate, analytical grade) were purchased from Sigma-Aldrich (St. Louis, Mo., USA). Sodium bicarbonate ($NaHCO_3$) and glacial acetic acid was purchased from Fisher Scientific (Pittsburgh, Pa., USA). Citrate-capped AuNPs colloids (50 nm) were purchased from NANO PARTZ™ Inc. (Loveland, Colo., USA). Organic baby spinach leaves were obtained from Whole Foods Market (Hadley, Mass., USA). Organic apples and grapes were purchased from Stop & Shop Supermarket (Hadley, Mass., USA). All reagents were used without further purification. Ultrapure water (18.2 MΩ·cm) was produced using a Thermo Scientific Barnstead Smart2Pure Water Purification System (Waltham, Mass., USA) and used for the preparation of all solutions.

Each test pesticide stock solution of 1000 mg/L was prepared with ultrapure water and methanol (v/v, 1:1) and further diluted to desired concentrations with ultrapure water prior to use. A 50 μL aliquot of each pesticide solution was mixed with 50 μL of a 250 mg/L solution of 50 nm AuNPs for 1 h at room temperature to ensure effective pesticide complexation with AuNPs through Au-thiol or Au-amino bond. A 5 μL aliquot of each of the pre-prepared pesticide/AuNPs solutions was pipetted onto fresh produce situated on a glass slide and air-dried in a fume hood for 10 min. Solutions of AuNPs without pesticide and each pesticide alone were also pipetted onto fresh produce as control treatments for comparison. A 5 μL aliquot of either the pre-prepared pesticide/AuNPs solution or AuNPs solution without pesticide were also pipetted onto a gold slide and dried for 10 min in a hood for comparison. Raman spectra were collected individually for all treatments.

In order to analyze the penetration depth of 50 nm AuNPs after placing them onto the external surfaces of different fresh produce, a 1 mL aliquot of a 20 mg/L ferbam solution was mixed with a 1 mL aliquot of a 250 mg/L AuNPs solution for 30 min to form ferbam/AuNPs complex. A 5 μL aliquot of the mixture was pipetted onto apple, grape and spinach, respectively. After air drying for 1 h, SERS depth mapping images were obtained using a confocal Raman instrument.

Organic apples were carefully hand washed with ultrapure water for 3 min and air-dried before experiment to remove surface contaminants. Then a 5 μL aliquot from a 100 mg/L solution of each pesticide was pipetted onto the apple surface. After air-drying the pesticides, apple peels with ~2.0×2.0 $cm^2$ area were cut from each treated apple using a sharp knife. To determine pesticide penetration with penetrative AuNPs, any interference caused by pesticide residues on the apple surface were removed by washing. Two different washing methods were investigated using either an acetic acid- or $NaHCO_3$-containing solution. Each peel was immersed into 20 mL of either a 5% acetic acid or a 1% $NaHCO_3$ solution for different times and gently rinsed with 200 mL of deionized water for 10 s, respectively. All washed samples were air-dried at room temperature for 10 min before being treated with AuNPs. After drying AuNPs for 1 h, SERS detection was performed on that area to evaluate washing effects. Ten discrete locations were randomly chosen on each apple peel sample and scanned. Similar samples were prepared without either washing method and were scanned as above for comparisons.

The penetration behavior of each pesticide on apples was monitored over different time periods from 30 min to 2 days. A 5 μL aliquot from each of the 100 mg/L pesticide solutions was pipetted onto apples and allowed to dry in air at room temperature over different time intervals (30 min, 6 h, 24 h and 48 h). Following drying, the surface residues from each applied pesticide were washed off using either the $NaHCO_3$ or acetic acid solution and a 5 μL aliquot of the 250 mg/L AuNPs solution was added as described above. After 1 h of drying, SERS depth mapping images were obtained using the confocal Raman instrument.

Organic grapes and spinach leaves were carefully hand washed as described above for apples before experiment to remove surface contaminants. In order to study pesticide penetration in grapes, the same two washing methods were used as presented above for apples. Grapes treated with each pesticides solution (100 mg/L) were washed with either a 5% acetic acid or 1% $NaHCO_3$ solution. Washing effects were evaluated using the SERS methods and the penetration behaviors of each pesticide were monitored as for apple above. Pesticides penetration experiments on spinach leaves were carried out as described above for apple and grape.

A DXR Raman microscope (Thermo Fisher Scientific, Madison, Wis., USA) with a 780 nm laser and a 20× long distance microscope objective was used in this study. Each sample was scanned from 400 to 2000 $cm^{-1}$ for a 2 s exposure time. For measuring pesticides on both gold slides and fresh produce surfaces, Raman mapping was carried out using a 50 μm slit aperture and 5 mW laser power to maximize the signals. Ten discrete locations were randomly chosen on each sample for analysis. For penetration studies, SERS depth mapping images were obtained using a 50 μm pinhole aperture and 1 mW laser power to control the confocal depths using a scanning depth of 300 μm. Each depth scanning vertical to produce surface was randomly selected in apple peel, grape peel or spinach leaf with an area of 100 μm×300 μm. The step size of the depth mapping was 20 μm and one image contained 75 scanning spots. Raman images were integrated based on the characteristic peaks in the pesticide spectra using the Atlμs Function in the OMINCS software (Thermo Fisher Scientific). Statistical analysis was conducted using SPSS Statistics 22 software (IBM Corporation, Armonk, N.Y., USA). The differences among results were calculated using an analysis of variance (ANOVA) and a post hoc Duncan test with a confidence level of 95%.

In order to study the penetration behaviors of pesticides, it is necessary to determine the characteristic peaks of each pesticide used in SERS mapping, and also to determine the detection limits and penetration depth limits of the method.

The characteristic SERS peaks of thiabendazole were detected at 1575, 1275, 1010 and 780 $cm^{-1}$, acetamiprid at 1110 and 633 $cm^{-1}$, ferbam at 1373, 1138, 936 and 550 $cm^{-1}$ and phosmet at 1192, 1015, 610 and 508 $cm^{-1}$. AuNPs alone resulted in only very small signals which could be considered negligible. Each pesticide was also investigated with or without AuNPs on fresh produce surface. When mixed with AuNPs each pesticide produced its characteristic SERS peaks on apple, grape and spinach leaf surface, and little or no Raman signals were obtained from all three fresh produce themselves. By contrast, there were no measurable Raman signals observed from each pesticide on fresh produce in the absence of AuNPs. In addition, no Raman signals were detected from AuNPs alone on each fresh produce. The SERS peaks at 1010 $cm^{-1}$ for thiabendazole, 633 $cm^{-1}$ for acetamiprid, 1373 $cm^{-1}$ for ferbam and 610 $cm^{-1}$ for phosmet were chosen as the characteristic peaks on each fresh produce, except 550 $cm^{-1}$ for ferbam on grape, monitoring and image integration in the following studies due to their prominent intensities. The use of SERS peak at 550 $cm^{-1}$ for ferbam on grape is due to the fact that the inherent Raman peak of grape at 1371 $cm^{-1}$ overlapped with the SERS peak of ferbam at 1373 $cm^{-1}$. Even as low as µg/L (ppb) levels, the SERS signals of all test pesticides can still be seen, indicating a high sensitivity of the SERS method for the detection of pesticides on tested fresh produce.

In order to accurately and reliably determine the penetration behaviors of pesticides, the penetration depth of AuNPs into different fresh produce was initially investigated. Ferbam served as an ideal indicator to monitor the penetration depth of AuNPs in selected fresh produce by using ferbam/AuNPs complex. Using this approach, it was found that AuNPs could penetrate into apple, grape and spinach to depths of approximately 220 µm, 180 µm and 275 µm, respectively after a 1 h incubation. These depths are enough further for the study of pesticides penetration as discussed later.

The concentration of pesticides applied was 100 mg/L, which was lower than the recommended label rate of pesticides (typically 600 mg/L) but have the same order of magnitude, to mimic the early stage of pesticide practical applications. From a viewpoint of useful guidance for effective and safe applications of pesticides on fresh produce, it is important and meaningful to monitor penetration of pesticide with a higher concentration. Prior to the application of penetrative AuNPs, surface pesticide residues were removed for the accurate determination of pesticide penetration behaviors; otherwise, co-penetration of the ferbam and AuNPs can confound results Different washing methods were investigated to ensure complete removal of the surface pesticide residues on the apple. SERS signals of thiabendazole disappeared and the intensity of characteristic peak of thiabendazole at 1010 $cm^{-1}$ was very weak after washing with the $NaHCO_3$ solution for 12 min, which indicated that the surface residues of thiabendazole was less than 2 µg/mL and could be considered negligible. As for the acetamiprid and phosmet, their SERS disappeared and the Raman intensity of characteristic SERS peaks of acetamiprid at 633 $cm^{-1}$ and phosmet at 610 $cm^{-1}$ were very weak after washing with the 1% $NaHCO_3$ solution were of for 8 min and 15 min, respectively, again indicating that surface pesticide residues were almost completely removed. In the case of ferbam removal, the 1% $NaHCO_3$ solution was not effective even after washing for 20 min. However, after washing for 10 min using the 5% acetic acid solution, the SERS signals of ferbam were absent, indicating almost total elimination of surface residues.

Using these washing methods, the penetration of each of the four test pesticides following different exposure times (30 min-48 h) were evaluated on apples using SERS mapping techniques. All pesticide penetrated into apples after a 48 h exposure. The corresponding SERS spectra of positions 1 to 4 from the SERS mapping images show the diagnostic fingerprint for each pesticide. The penetration of the two systemic pesticides, thiabendazole and acetamiprid, were observed after a 30 min exposure and the penetration depth gradually increased to approximately 160 µm for thiabendazole and 140 µm for acetamiprid after a 48 h exposure. The terminal depth can depend on the color change from light blue to dark blue on each Raman mapping image. In comparison, the non-systemic pesticides, ferbam and phosmet, were first detected following a 6 h exposure. After 48 h, the penetration depths slowly increased to approximately 80 µm for ferbam and 55 µm for phosmet. These findings were unexpected because non-systemic pesticides should have little or no penetration ability. The detection of non-systemic pesticides is significant because internalized pesticides are less likely to be eliminated during postharvest processes and may present greater risks to public health. Until now, there has been no disclosure reporting that non-systemic pesticide can penetrate deeply into fresh produce. The two systemic pesticides penetrated faster than the two non-systemic pesticides and they penetrated deeper than the two non-systemic pesticides after 48 h exposure. Between the two systemic pesticides, thiabendazole penetrated statistically deeper than acetamiprid after 48 h. There is no difference between the two non-systemic pesticides in terms of penetration depth in the initial 6 h. However, Ferbam penetrated statistically deeper than phosmet after 24 h and 48 h exposure.

Overall the penetration of pesticides on grape was similar to that on apple. Initially different washing methods were evaluated to insure total removal of each pesticide from grape surface. The best washing treatments for removing thiabendazole, acetamiprid or phomet were 1% $NaHCO_3$ washing solution for 15 min, 10 min and 18 min, respectively. For elimination of surface ferbam residues, the best treatment was the 5% acetic acid washing method for 15 min. Subsequently, the penetration behavior for each pesticide was examined by the SERS mapping method. The corresponding SERS spectra from positions 1 to 4 using the SERS mapping images (48 h exposure) clearly show the Raman fingerprint of each pesticide The penetration of thiabendazole or acetamiprid was apparent after 30 min exposure and the overall penetration ability for acetamiprid (about 75 µm in depth) was superior to thiabendazole (about 55 µm in depth) on grapes after 48 h. The penetration of the non-systemic pesticides, ferbam and phosmet, were observed only after 48 h and both of their penetration degrees were shallow (about 20 µm depth). Overall, the two systemic pesticides penetrated faster and deeper than the two non-systemic pesticides. Between the two systemic pesticides, acetamiprid penetrated statistically deeper than thiabendazole all the time. No significant difference was observed between the two non-systemic pesticides in terms of penetration depth.

Similar to apple and grape, surface residues of thiabendazole, acetamiprid and phosmet were not detected following washing with the 1% $NaHCO_3$ solution for 10 min, 3 s and 10 min, respectively. Surface residues of ferbam were removed by washing with 5% acetic acid solution for 10 min. Following the removal of external pesticide residues using the best washing method for removal each pesticide, SERS depth mapping images were used to investigate pesticide penetration. The systemic pesticide thiabendazole was detected after a 30 min exposure as seen from the SERS mapping image and penetrated to a depth of ~220 μm by 48 h, indicating that thiabendazole penetrated rapidly and extensively into spinach. In comparison, the other systemic pesticide acetamiprid only penetrated to a depth of 90 μm after a 48 h exposure. The non-systemic pesticide ferbam penetrated to 30 μm after 48 h. This result differs from a previous study where a 20 mg/L ferbam concentration was used and no internalized signal was observed, which may indicate a concentration-dependent penetration behavior for ferbam. The other non-systemic pesticide phosmet was detected following a 24 h exposure and penetrated to a depth of 70 μm at 48 h. Again, the two systemic pesticides have significantly stronger ability for penetration then non-systemic pesticides. Thiabendazole penetrated the most and ferbam penetrated the least. It should be noted that in each fresh produce tested (apple, grape and spinach leaf), the penetration depth of each pesticide was lower than that of AuNPs, indicating that AuNPs appear to be effective and reliable probes for the study of pesticide penetration.

Pesticide penetration into fresh produce is a complex process, depending on surface characters of fresh produce, the physicochemical properties of the pesticides and environmental conditions such as temperature or humidity. At 30 min, only systemic pesticides were detected in the fresh produce. Particularly, thiabendazole penetrated to a depth of 100 μm into spinach by such a short time. Two non-systemic pesticides were only detected in apples after 6 h. Phosmet was firstly detected in spinach after 24 h. After 24 h, the penetration depths of thiabendazole for apples and spinach (about 140 and 160 μm) were significantly larger than its depth for grape which was only to about 36 μm. After 48 h, both non-systemic pesticides were first detected in grapes, and ferbam was firstly detected in spinach. This data suggests the penetration behavior for each pesticide is varied based on the nature of pesticide and the matrices of the fresh produce. Generally speaking, systemic pesticides can penetrate into fresh produce faster and deeper (after 48 h exposure) than non-systemic pesticides. Grapes appear to be the most difficult matrix for pesticide penetration.

The different penetration ability on fresh produce is possibly because the differences of cuticle and epicuticular wax on fresh produce. The plant cuticle including of a polymeric cutin matrix and soluble waxes is a nonliving and non-uniform plant structure which acts as a barrier against foreign substance. The cuticle extracellular membrane is composed of cutin and waxes. The cuticular membranes of fruits are generally thicker than those of leaves).

Example 3

Further details of this Example can be found in "Investigation of Pesticide Penetration and Persistence on Harvested and Live Basil Leaves using Surface-Enhanced Raman Scattering Mapping", *J. Agric. Food Chem.* 2017, 65, 3541-3550, the contents of which, including supplemental materials referred to therein are hereby incorporated by reference. Thiabendazole (systemic fungicide: 2-(4-thiazolyl)-1H-benzimidazole, ≥99%, analytical grade) and ferbam (non-systemic fungicide: Iron(III) dimethyl dithiocarbamate, analytical grade) were purchased from Sigma-Aldrich (St. Louis, Mo., USA). Citrate-capped AuNPs colloids (50 nm) were purchased from NANO PARTZ™ Inc. (Loveland, Colo., USA). Au-coated glass slides were purchased from Fisher Scientific (Pittsburgh, Pa.). USDA organic basil plants were purchased from Stop & Shop Supermarket (Hadley, Mass., USA). All reagents were used without further purification. Ultrapure water (18.2 MΩ·cm) was produced using a Thermo Scientific Barnstead Smart2Pure Water Purification System (Waltham, Mass., USA) and used for the preparation of all solutions.

To study the penetration behaviors of pesticides, it was necessary to determine the characteristic peaks of each pesticide used in SERS mapping and to determine the detection limits and penetration depth limits of the method. In this study, 50 nm AuNPs were used as probes for the investigation of pesticide behavior due to their ability to penetrate plant leaves effectively and to enhance SERS signal based on our previous study.

Stock solutions of each test pesticide (1000 mg/L, ppm) were prepared using ultrapure water and methanol (v/v, 1:1) and further diluted to desired concentrations with ultrapure water prior to use. A 50 μL aliquot of each pesticide solution was mixed with 50 μL of a 250 mg/L solution of 50 nm AuNPs in a tube by gentle pipetting for 30 s and then placed at room temperature undisturbed for 1 h to ensure effective pesticide complexation with AuNPs through Au-thiol or Au-amino bond. A 5 μL aliquot from one of the pre-prepared pesticide/AuNPs solutions was pipetted onto the top surface of a single basil leave situated on a glass slide and air-dried in a fume hood for 10 min. Solutions of AuNPs without pesticide and each pesticide alone were also pipetted onto individual basil leaves as control treatments for comparison proposes. Ten discrete locations were randomly chosen on each individual leaf for Raman analysis and each leaf sample had two duplicates. Raman spectra were collected individually for all samples.

To analyze the penetration depth of 50 nm AuNPs after 30 min exposure, a Raman indicator for tracking of AuNPs was first selected. 10 mg/L of ferbam was used as the Raman indicator because it met two requirements. First, ferbam was very SERS active which produced strong SERS signals to facilitate tracking AuNPs penetration. Second, preliminary results showed that 10 mg/L of ferbam does not penetrate into basil leaves following a 30-min exposure thus it cannot interfere with AuNPs penetration. In detail, after placing each pesticide onto the external surfaces of harvested or live basil leaves, a 1 mL aliquot of a 10 mg/L ferbam solution was mixed with a 1 mL aliquot of a 250 mg/L AuNPs solution in a tube for 30 min in the room temperature to form ferbam/AuNPs complex. A 5 μL aliquot of the mixture was pipetted onto harvested leaves or onto the live leaves on the plant. After air drying for 30 min, SERS depth mapping images were obtained using a confocal Raman instrument as detailed below.

For the study of pesticide penetration into live basil leaves, 36 intact leaves (approximately 0.2 g per leaf) were selected from six live plants as the experimental target (6 leaves per plant) and carefully rinsed with 450 mL ultrapure water for 30 s and air-dried before the experiment to remove surface contaminants like dust. After rinsing, the clean leaves were used to study of pesticide penetration. The penetration behavior of each pesticide into live leaves was monitored over different time periods at 30 min, 24 h, and 48 h. A 5 μL aliquot of a 10 mg/L solution of each pesticide was pipetted onto the top surface of individual leaf and allowed to dry in air at room temperature over different time intervals (30 min, 24 h and 48 h) (Step 1). Some of the pesticides might penetrate into leaves from the surface during the periods. After pesticide penetrated into leaves for different time periods, ultrapure water with flow rate of 15 mL/s was utilized to gently rinse the surface of leaves (Step 2). Different rinsing times were then investigated to complete removal of each pesticide residue on the surface. After rinsing of surface pesticide residues, all leaf samples were air-dried at room temperature for 30 min. A 5 µL aliquot of a 250 mg/L solution of AuNPs was then pipetted onto the same area of the basil leaves where the pesticide solution had been placed (Step 3). The video camera in the Raman microscope was used to record the position on the leaves and help to find the same area for AuNPs deposition. After AuNPs treatment for drying 30 min, SERS detection was performed on that area using the confocal Raman instrument. Each treatment was performed twice.

For the study of the pesticides penetration on harvested basil leaves, 36 intact leaves (0.2 g per leaf) were first cut off from petiole on live plants using a sharp knife and carefully rinsed as described above for live leaves. During the experiment, the stems of each harvested leaf were immersed into water to keep the leaf fresh. To study pesticide penetration into harvested leaves, the same rinsing method and pesticides penetration protocols were carried out as described above for live leaves.

For monitoring the persistence of pesticides in live leaves over time, a 5 µL aliquot from each of the 10 mg/L pesticide solutions was individually pipetted onto a single leaf and allowed to dry in air at room temperature. Different growing time intervals were used to investigate each pesticide behaviors with thiabendazole (30 min, 1 week, 2 weeks and 3 weeks) and ferbam (24 h, 1 week, 2 week and 3 weeks). The first growing intervals of thiabendazole at 30 min and ferbam at 24 h were different. This was because 30-min exposure and 24-h exposure was the first time when thiabendazole and ferbam were able to penetrate into leaves, respectively. After growing over different time intervals, the surface residues from each applied pesticide were rinsed off using water and a 5 µL aliquot of the 250 mg/L AuNPs solution was added on the same position. After 30 min of drying, SERS depth mapping images were obtained using the confocal Raman instrument.

A DXR Raman microscope (Thermo Fisher Scientific, Madison, Wis., USA) with a 780-nm laser and a 20× long distance microscope objective was used in this study. Each sample was scanned from 400 to 2000 $cm^{-1}$ for a 2-s exposure time.

For detecting pesticides on basil leaf surfaces, Raman spectra were carried out using a 50 µm slit aperture and 3 mW laser power to maximize the signals. In the area of each dried droplet of AuNPs solution on a leaf, ten discrete locations from the area were chosen and scanned through the Raman microscope. Their SERS spectra were analyzed with TQ Analyst (version 8.0). The final SERS spectrum of each area was averaged by ten independent SERS spectra coming from ten discrete locations. The variances of SERS spectral data between spots and samples were assessed by principal component analysis (PCA).

For penetration studies, SERS depth mapping images were obtained using a 50 µm pinhole aperture and 3 mW laser power to control the confocal depth using a scanning depth of 300 µm. Each depth area (100 µm×300 µm) was chosen from the treated spot on the leaf distant from a gland because the gland is the cavity, not a flat surface. The step size of the depth mapping was 20 µm and one image contained 75 scanning spots. Raman images were integrated based on the characteristic peaks in the pesticide spectra using the Atlµs Function in the OMINCS software (Thermo Fisher Scientific). There was one spot on each leaf and one depth area was selected from each spot. For each pesticide depth mapping experiment, there were six duplicates with six leaves coming from three different plants (2 leaves from each plant). Statistical analysis was conducted using SPSS Statistics 22 software (IBM Corporation, Armonk, N.Y., USA). The differences among results were calculated using an independent sample T-test or analysis of variance (ANOVA) and a post hoc Duncan test with a confidence level of 95%.

The SERS spectra of thiabendazole and ferbam in the presence of AuNPs were obtained on Au-coated microscopic slides and on non-rinsed basil leaf surface. The fingerprint information of each pesticide in the presence of AuNPs is clearly evident on the leaf's surface. The peaks at 1010 $cm^{-1}$ of thiabendazole and 1371 $cm^{-1}$ of ferbam were chosen as the characteristic peaks for monitoring and SERS mapping in the following studies.

The controls were leaves without pesticide being applied. Even as low as µg/L levels of pesticide solutions, SERS signals of the test pesticides were clearly seen, showing the ultra-high sensitivity of the currently developed SERS method for the detection of pesticides on plant leaves in situ.

To accurately and reliably determine the penetration behaviors of pesticides into leaves, we need to determine the penetration depth of AuNPs alone (uncomplexed with pesticide) as well as to determine the most efficient and complete method to remove surface pesticide residues. The penetration depth of AuNPs alone using live or harvested leaves was determined to be approximately 245 µm and 180 µm, respectively, after a 30-min incubation, which was about 30% of the leave thickness. Different methods were then evaluated to ensure the complete removal of surface pesticide residues. We found that the SERS signals of surface thiabendazole and ferbam residues were not detected after rinsing with ultrapure water for 8 s and 5 s, respectively, indicating that the concentration of surface residues of thiabendazole and ferbam were lower than 5 µg/L and 10 µg/L, respectively, which could be considered negligibly. Interestingly, these pesticides were easier to remove from basil leaf surfaces when compared with other fresh produce, such as spinach, apple peel or grape peel, when rinsed by water. This finding is probably due, in part, to the specific leaf structure of basil. Basil is an annual aromatic herb belonging to the Lamiaceae family. Like other members of the Lamiaceae, basil leaves have two types of glandular trichomes on their surface, termed peltate and capitate glands, which usually produce volatile oils. When the leaves were held up to light, many tiny glandular structures in the leaves could be seen, which look like holes. Based on a previous study, the glands can recess into the surface of the leaf and develop as a cavity. The thiabendazole signals are highest around the cavity denoting the gland, which means pesticide tends to accumulate around the gland. The specific cavity structure of basil leaves likely increases the surface area, which would augment the interaction between water and pesticide residues and thus facilitated the pesticide removal.

After removing surface residues, the penetration of each pesticide following different exposure times (30 min to 48 h) was evaluated on either harvested or live leaves using SERS mapping technique. The mapping images were collected from an area of the leaf that was far away from glands to ensure reliable penetration results because the gland area is not a flat surface. The systemic pesticide thiabendazole penetrated into both harvested and live leaves following a 30-min exposure. With increasing exposure time, the penetration depths of thiabendazole gradually increased to approximately 180 μm on harvested leaves and 225 μm on live leaves at 48-h after exposure, indicating that thiabendazole penetrated deeper into live leaves versus harvested leaves. Ferbam was first detected on harvested leaves after 48 h at a depth of 18 μm, while ferbam on live leaves was first detected at 24 h at a depth of about 50 μm, which increased to 130 μm by 48 h. Similar as with thiabendazole, ferbam penetrated deeper into live leaves versus harvested leaves. This finding may be due, in part, to the higher level of transpiration in live versus harvested leaves since they are still part of a living intact plant.

Pesticide penetration was investigated using both intact and damaged leaves on live plants. Damaged leaves were prepared using a sharp knife to scratch the top surface of intact leaves. Each of the damaged leaves had 20 scrapes on each leaf and the distance between each scrape is 0.2 cm. The penetration depth for thiabendazole applied on intact and damaged leaves was 170 and 80 μm, respectively. The decrease in the penetration depth of thiabendazole in damaged leaves could be the result, in part, of reduced translocation that occurs due to the structural disruption of the damaged leaf. Additionally, the physical damage used to disrupt the intact leaves may have induced certain enzymes, particularly, oxidative enzymes (e.g., cytochrome P450s, peroxidases, and polyphenol oxidases), which are known to metabolize pesticides.

To determine the effect of leaf age on penetration, old leaves were selected from plants grown for 45 days with an approximate weight of 0.204±0.019 g for each leaf and young leaves from plants grown for 15 days with an approximate weight 0.053±0.007 g for each leaf. Following a 24 h exposure, thiabendazole penetrated deeper into large leaves (165 μm) versus small leaves (95 μm). This result was probably due to the fact that older leaves have more and larger stomata cells, resulting in a higher transpiration rate and hence a deeper penetration.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

Additional Embodiments

The following exemplary embodiments are provided, the numbering of which is not to be construed as designating levels of importance:

Embodiment 1 provides a method for mapping one or more analytes contacting a biological structure using surface-enhanced Raman spectroscopy, the method comprising:

contacting the biological structure and a metallic nanoparticle;
collecting a spectrum with a Raman spectrometer; and
determining a location of the analyte along at least one of an x-direction, a y-direction and a z-direction on the structure.

Embodiment 2 provides the method of Embodiment 1, wherein the biological structure comprises a tissue.

Embodiment 3 provides the method of Embodiment 2, wherein the tissue is chosen from a plant tissue and an animal tissue.

Embodiment 4 provides the method of Embodiment 3, wherein the animal tissue is skin.

Embodiment 5 provides the method of Embodiment 3, wherein the plant tissue is a chosen from a leaf and a root.

Embodiment 6 provides the method of any one of Embodiments 1-5, wherein a particle size of the metallic nanoparticle is in a range of from about 20 nm to about 200 nm.

Embodiment 7 provides the method of any one of Embodiments 1-6, wherein a particle size of the metallic nanoparticle is in a range of from about 40 nm to about 60 nm.

Embodiment 8 provides the method of any one of Embodiments 1-7, wherein the metallic nanoparticle is substantially spherical.

Embodiment 9 provides the method of any one of Embodiments 1-8, wherein the metallic nanoparticle comprises a material chosen from $Ag_2O$, elemental silver, elemental gold, elemental copper, elemental platinum, alloys thereof, and mixtures thereof.

Embodiment 10 provides the method of any one of Embodiments 1-9, wherein the metallic nanoparticle is elemental gold.

Embodiment 11 provides the method of any one of Embodiments 1-10, further comprising a plurality of the metallic nanoparticles.

Embodiment 12 provides the method of Embodiment 11, wherein the plurality of the metallic nanoparticles comprise a mixture of metallic nanoparticles at least two of which comprising a different material.

Embodiment 13 provides the method of any one of Embodiments 11 or 12, wherein a first metallic nanoparticle has a particle size in a largest dimension that is different from a particle size in a largest dimension of a second nanoparticle.

Embodiment 14 provides the method of any one of Embodiments 1-13, wherein the analyte is a non-naturally occurring compound in the biological structure.

Embodiment 15 provides the method of any one of Embodiments 1-14, wherein the analyte is chosen from a pesticide an antibiotic, and a mixture thereof.

Embodiment 16 provides the method of Embodiment 15, wherein the pesticide is chosen from thiabendazole, ferbam, and mixtures thereof.

Embodiment 17 provides the method of any one of Embodiments 1-16, further comprising a mixture of the analytes wherein more than one of the analytes is in contact with the biological structure.

Embodiment 18 provides the method of Embodiment 17, wherein the mixture of analytes comprises a first analyte and a second analyte different from the first analyte.

Embodiment 19 provides the method of any one of Embodiments 1-18, further comprising positioning the metallic nanoparticle proximate to the analyte.

Embodiment 20 provides the method of any one of Embodiments 1-19, wherein a distance between an adjacent metallic nanoparticle and the analyte is in a range of from about 0.10 nanometers to about 20 nanometers.

Embodiment 21 provides the method of any one of Embodiments 1-20, wherein a distance between an adjacent metallic nanoparticle and the analyte is in a range of from about 0.10 nanometers to about 5 nanometers.

Embodiment 22 provides the method of any one of Embodiments 1-21, further comprising complexing the analyte and the metallic nanoparticle.

Embodiment 23 provides the method of any one of Embodiments 1-22, wherein the collecting of the spectrum and the contacting of the biological structure with the metallic nanoparticle occur at least partially simultaneously.

Embodiment 24 provides the method of any one of Embodiments 1-23, wherein the spectrum is collected following contacting the biological structure with the metallic nanoparticle.

Embodiment 25 provides the method of any one of Embodiments 1-24, further comprising collecting a second spectrum.

Embodiment 26 provides the method of any one of Embodiments 1-25, further comprising washing a surface of the biological structure with water before collecting the spectrum.

Embodiment 27 provides the method of any one of Embodiments 1-26, wherein the biological structure is a plant tissue, and the metallic nanoparticle is elemental gold.

Embodiment 28 provides a method for mapping one or more analytes that contact a biological structure via surface-enhanced Raman spectroscopy, the method comprising:
contacting the biological structure with at least one elemental gold nanoparticle;
collecting a spectrum with a Raman spectrometer; and
detecting a location of the analyte along at least one of an x-y direction and a z-direction on the structure.

Embodiment 29 provides an assembly comprising:
a plant tissue;
one or more analytes contacting the plant tissue;
at least one metallic nanoparticle that contacts the biological structure; and
a Raman microscope configured to detect a location of the analyte along at least one of an x-y direction and a z-direction on the structure.

Embodiment 30 provides the assembly of Embodiment 1, wherein the biological structure comprises a tissue.

Embodiment 31 provides the assembly of Embodiment 30, wherein the tissue is chosen from a plant tissue and an animal tissue.

Embodiment 32 provides the assembly of Embodiment 31, wherein the animal tissue is skin.

Embodiment 33 provides the assembly of Embodiment 31, wherein the plant tissue is a chosen from a leaf and a root.

Embodiment 34 provides the assembly of any one of Embodiments 29-33, wherein a particle size of the metallic nanoparticle is in a range of from about 20 nm to about 200 nm.

Embodiment 35 provides the assembly of any one of Embodiments 29-34, wherein a particle size of the metallic nanoparticle is in a range of from about 40 nm to about 60 nm.

Embodiment 36 provides the assembly of any one of Embodiments 29-35, wherein the metallic nanoparticle is substantially spherical.

Embodiment 37 provides the assembly of any one of Embodiments 29-36, wherein the metallic nanoparticle comprises a material chosen from $Ag_2O$, elemental silver, elemental gold, elemental copper, elemental platinum, alloys thereof, and mixtures thereof.

Embodiment 38 provides the assembly of any one of Embodiments 29-37, wherein the metallic nanoparticle is elemental gold.

Embodiment 39 provides the assembly of any one of Embodiments 29-38, further comprising a plurality of the metallic nanoparticles.

Embodiment 40 provides the assembly of Embodiment 39, wherein the plurality of the metallic nanoparticles comprise a mixture of metallic nanoparticles at least two of which comprising a different material.

Embodiment 41 provides the assembly of any one of Embodiments 39 or 40, wherein a first metallic nanoparticle has a particle size in a largest dimension that is different from a particle size in a largest dimension of a second nanoparticle.

Embodiment 42 provides the assembly of any one of Embodiments 29-41, wherein the analyte is a non-naturally occurring compound in the biological structure.

Embodiment 43 provides the assembly of any one of Embodiments 29-42, wherein the analyte is chosen from a pesticide, an antibiotic, and a mixture thereof.

Embodiment 44 provides the assembly of Embodiment 43, wherein the pesticide is chosen from thiabendazole, ferbam, and mixtures thereof.

Embodiment 45 provides the assembly of any one of Embodiments 29-44, further comprising a mixture of the analytes.

Embodiment 46 provides the assembly of Embodiment 45, wherein the mixture of analytes comprises a first analyte and a second analyte different from the first analyte.

Embodiment 47 provides the assembly of any one of Embodiments 29-46, wherein the metallic nanoparticle is positioned proximate to the analyte.

Embodiment 48 provides the assembly of any one of Embodiments 29-47, wherein a distance between an adjacent metallic nanoparticle and the analyte is in a range of from about 0.10 nanometers to about 20 nanometers.

Embodiment 49 provides the assembly of any one of Embodiments 29-48, wherein a distance between an adjacent metallic nanoparticle and the analyte is in a range of from about 0.10 nanometers to about 5 nanometers.

Embodiment 50 provides the assembly of any one of Embodiments 29-49, wherein the one or more analytes and the at least one metallic nanoparticle are complexed.

What is claimed is:

1. A method for mapping one or more analytes contacting a biological structure using surface-enhanced Raman spectroscopy, the method comprising:
contacting the biological structure and a metallic nanoparticle;
allowing the metallic nanoparticle to penetrate the biological structure substantially in the z-direction;
collecting a spectrum of the one or more analytes with a Raman spectrometer; and
determining a location of the one or more analytes along a depth in a z-direction and at least one of an x-direction and a y-direction in the biological structure,
wherein a distance between the one or more analytes and an adjacent metallic nanoparticle is in a range of from about 0.10 nm to about 20 nm and determining the location of the one or more analytes along the depth in the z-direction comprises the Raman spectrometer scanning the biological structure at a predetermined depth.

2. The method of claim 1, wherein the biological structure comprises a tissue.

3. The method of claim 1, wherein a particle size of the metallic nanoparticle is in a range of from about 20 nm to about 200 nm.

4. The method of claim 1, wherein the metallic nanoparticle comprises a material chosen from $Ag_2O$, elemental silver, elemental gold, elemental copper, elemental platinum, alloys thereof, and mixtures thereof.

5. The method of claim 1, further comprising a plurality of the metallic nanoparticles.

6. The method of claim 5, wherein a first metallic nanoparticle has a particle size in a largest dimension that is different from a particle size in a largest dimension of a second nanoparticle.

7. The method of claim 1, wherein the one or more analytes is a non-naturally occurring compound in the biological structure.

8. The method of claim 1, wherein the one or more analytes is chosen from a pesticide, an antibiotic, and a mixture thereof.

9. The method of claim 1, further comprising positioning the metallic nanoparticle proximate to the one or more analytes.

10. The method of claim 1, further comprising complexing at least some of the one or more analytes and the metallic nanoparticle.

11. The method of claim 1, wherein the collecting of the spectrum and the contacting of the biological structure with the metallic nanoparticle occur at least partially simultaneously.

12. The method of claim 1, wherein the spectrum is collected following contacting the biological structure with the metallic nanoparticle.

13. The method of claim 1, further comprising collecting a second spectrum.

14. The method of claim 1, further comprising washing a surface of the biological structure with water before collecting the spectrum.

15. A method for mapping one or more analytes contacting a biological structure via surface-enhanced Raman spectroscopy, the method comprising:

contacting the biological structure with at least one elemental gold nanoparticle;

allowing the at least one elemental gold nanoparticle to penetrate the biological structure substantially in a z-direction;

collecting a spectrum of the one or more analytes with a Raman spectrometer; and determining a location of the one or more analytes along a depth in a z-direction and at least one of an x-direction and a y-direction the structure, wherein a distance between the one or more analytes and an adjacent at least one elemental gold nanoparticle is in a range of from about 0.10 nm to about 20 nm and determining the location of the one or more analytes along the depth in the z-direction comprises the Raman spectrometer scanning the biological structure at a predetermined depth.

16. An assembly comprising:

a biological tissue;

one or more analytes contacting the biological tissue;

at least one metallic nanoparticle that contacts the biological tissue; and a Raman microscope configured to detect a location of the one or more analytes along a depth in a z-direction and at least one of an x-direction and a y-direction in the biological structure by scanning the biological tissue at a predetermined depth.

17. The assembly of claim 16, wherein the metallic nanoparticle comprises a material chosen from $Ag_2O$, elemental silver, elemental gold, elemental copper, elemental platinum, alloys thereof, and mixtures thereof.

18. The assembly of claim 16, wherein the biological tissue comprises a plant tissue or an animal tissue.

19. The assembly of claim 18, wherein the tissue is a plant tissue.

20. The assembly of claim 16, wherein the one or more analytes is chosen from a pesticide, an antibiotic, and a mixture thereof.

* * * * *